(12) United States Patent
Menk et al.

(10) Patent No.: US 9,132,007 B2
(45) Date of Patent: Sep. 15, 2015

(54) ANTI-PARAVALVULAR LEAKAGE COMPONENTS FOR A TRANSCATHETER VALVE PROSTHESIS

(71) Applicant: Medtronic CV Luxembourg S.a.r.l., Luxembourg (LU)

(72) Inventors: Ana Menk, Saint Paul, MN (US); Scott Mosher, Santa Rosa, CA (US)

(73) Assignee: Medtronic CV Luxembourg S.a.r.l., Luxembourg (LU)

( * ) Notice: Subject to any disclaimer, the term of this patent is extended or adjusted under 35 U.S.C. 154(b) by 30 days.

(21) Appl. No.: 13/738,376

(22) Filed: Jan. 10, 2013

(65) Prior Publication Data

US 2014/0194981 A1 Jul. 10, 2014

(51) Int. Cl.
*A61F 2/24* (2006.01)

(52) U.S. Cl.
CPC ............... *A61F 2/2418* (2013.01); *A61F 2/246* (2013.01); *A61F 2/2409* (2013.01); *A61F 2/2412* (2013.01); *A61F 2/2439* (2013.01); *A61F 2220/0075* (2013.01); *A61F 2230/005* (2013.01); *A61F 2230/0054* (2013.01); *A61F 2250/001* (2013.01); *A61F 2250/0003* (2013.01);
(Continued)

(58) Field of Classification Search
CPC ....... A61F 2/24; A61F 2/2409; A61F 2/2412; A61F 2/2418; A61F 2/2442; A61F 2/2445
USPC ...................... 623/1.24, 1.26, 2.1, 2.12–2.19, 623/2.36–2.38
See application file for complete search history.

(56) References Cited

U.S. PATENT DOCUMENTS

| 5,571,175 A | 11/1996 | Vanney et al. |
| 7,276,078 B2 | 10/2007 | Spenser et al. |

(Continued)

FOREIGN PATENT DOCUMENTS

| EP | 0537487 | 4/1993 |
| WO | WO2009/094501 | 7/2009 |

(Continued)

OTHER PUBLICATIONS

"Invitation to Pay Additional Fees", International application No. PCT/US2014/010734, including annex with Partial International Search Report, dated Apr. 9, 2014.

(Continued)

*Primary Examiner* — Andrew Iwamaye
*Assistant Examiner* — Leslie Lopez

(57) ABSTRACT

A valve prosthesis includes one or more anti-paravalvular leakage components coupled to a stent. The anti-paravalvular leakage component may encircle the stent and include a radially expandable control ring coupled to an unattached edge of a flexible skirt which extends the unattached skirt edge outwardly away from the stent and against the native heart valve to form an open-ended annular pocket around the stent. The anti-paravalvular leakage component may encircle the perimeter of the stent and include a flexible skirt having opposing edges coupled to the stent to form one or more enclosed compartments around the stent. Each compartment includes a one-way valve which allows for blood flow into the compartment but prevents blood flow out of the compartment. The anti-paravalvular leakage component may be at least one flap that is coupled to an inner surface of the stent and formed of a flexible material moveable by blood flow.

6 Claims, 10 Drawing Sheets

(52) U.S. Cl.
CPC  *A61F 2250/0039* (2013.01); *A61F 2250/0069* (2013.01); *A61F 2250/0071* (2013.01)

(56) References Cited

U.S. PATENT DOCUMENTS

| | | | |
|---|---|---|---|
| 7,331,991 B2 | 2/2008 | Kheradvar et al. | |
| 7,628,805 B2 | 12/2009 | Spenser et al. | |
| 7,708,775 B2 | 5/2010 | Rowe et al. | |
| 7,780,725 B2 | 8/2010 | Haug et al. | |
| 8,002,825 B2 | 8/2011 | Letac et al. | |
| 8,182,528 B2 | 5/2012 | Salahieh et al. | |
| 8,231,670 B2 | 7/2012 | Salahieh et al. | |
| 8,449,599 B2 | 5/2013 | Chau et al. | |
| 8,603,160 B2 | 12/2013 | Salahieh et al. | |
| 8,623,078 B2 | 1/2014 | Salahieh et al. | |
| 8,628,566 B2 | 1/2014 | Eberhardt et al. | |
| 8,641,757 B2 | 2/2014 | Pintor et al. | |
| 8,668,733 B2 | 3/2014 | Salahieh et al. | |
| 8,673,000 B2 | 3/2014 | Tabor et al. | |
| 8,734,484 B2 | 5/2014 | Ahlberg et al. | |
| 8,795,357 B2 | 8/2014 | Yohanan et al. | |
| 8,801,706 B2 | 8/2014 | Rothstein et al. | |
| 8,808,356 B2 | 8/2014 | Braido et al. | |
| 2003/0199963 A1 | 10/2003 | Tower et al. | |
| 2003/0199971 A1 | 10/2003 | Tower et al. | |
| 2004/0030381 A1* | 2/2004 | Shu | 623/2.11 |
| 2004/0111111 A1 | 6/2004 | Lin | |
| 2004/0122514 A1 | 6/2004 | Fogarty et al. | |
| 2006/0004442 A1 | 1/2006 | Spenser et al. | |
| 2007/0293944 A1 | 12/2007 | Spenser | |
| 2008/0243245 A1 | 10/2008 | Thambar | |
| 2009/0099653 A1 | 4/2009 | Suri et al. | |
| 2009/0112311 A1 | 4/2009 | Miles et al. | |
| 2009/0192591 A1 | 7/2009 | Ryan et al. | |
| 2010/0036479 A1 | 2/2010 | Hill et al. | |
| 2010/0168844 A1 | 7/2010 | Toomes et al. | |
| 2010/0198238 A1 | 8/2010 | Sorajja | |
| 2010/0280589 A1* | 11/2010 | Styrc | 623/1.12 |
| 2011/0054466 A1 | 3/2011 | Rothstein et al. | |
| 2011/0098802 A1* | 4/2011 | Braido et al. | 623/1.26 |
| 2011/0137397 A1 | 6/2011 | Chau et al. | |
| 2011/0172765 A1 | 7/2011 | Nguyen et al. | |
| 2011/0245911 A1 | 10/2011 | Quill et al. | |
| 2011/0257721 A1 | 10/2011 | Tabor | |
| 2011/0264206 A1 | 10/2011 | Tabor | |
| 2012/0022633 A1 | 1/2012 | Olson et al. | |
| 2012/0041549 A1 | 2/2012 | Salahieh et al. | |
| 2012/0041550 A1 | 2/2012 | Salahieh et al. | |
| 2013/0190857 A1 | 7/2013 | Mitra et al. | |
| 2013/0190862 A1 | 7/2013 | Pintor et al. | |
| 2013/0197622 A1 | 8/2013 | Mitra et al. | |
| 2013/0331929 A1 | 12/2013 | Mitra et al. | |
| 2014/0046426 A1 | 2/2014 | Kovalsky | |
| 2014/0114402 A1 | 4/2014 | Ahlberg et al. | |
| 2014/0114406 A1 | 4/2014 | Salahieh et al. | |
| 2014/0194975 A1 | 7/2014 | Quill et al. | |
| 2014/0194981 A1 | 7/2014 | Menk et al. | |
| 2014/0222144 A1 | 8/2014 | Eberhardt et al. | |
| 2014/0236287 A1 | 8/2014 | Clague et al. | |
| 2014/0243966 A1 | 8/2014 | Garde et al. | |
| 2014/0243969 A1 | 8/2014 | Venkatasubramanian et al. | |
| 2014/0257475 A1 | 9/2014 | Gross et al. | |
| 2014/0277388 A1 | 9/2014 | Skemp | |
| 2014/0277413 A1 | 9/2014 | Richter et al. | |
| 2014/0277417 A1 | 9/2014 | Schraut et al. | |
| 2014/0277419 A1 | 9/2014 | Garde et al. | |
| 2014/0277423 A1 | 9/2014 | Alkhatib et al. | |
| 2014/0277424 A1 | 9/2014 | Oslund | |
| 2014/0277425 A1 | 9/2014 | Dakin | |
| 2014/0277426 A1 | 9/2014 | Dakin et al. | |
| 2014/0277428 A1 | 9/2014 | Skemp et al. | |

FOREIGN PATENT DOCUMENTS

| | | |
|---|---|---|
| WO | WO2011/051043 | 5/2011 |
| WO | WO2013/033791 | 3/2013 |
| WO | WO2013/059747 | 4/2013 |
| WO | WO2014072439 | 5/2014 |

OTHER PUBLICATIONS

"International Search Report and Written Opinion", International Application No. PCT/2014/014090, mailed Apr. 14, 2014.

* cited by examiner

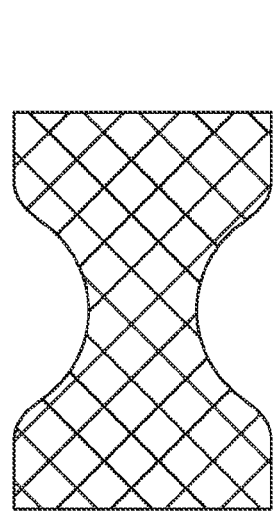
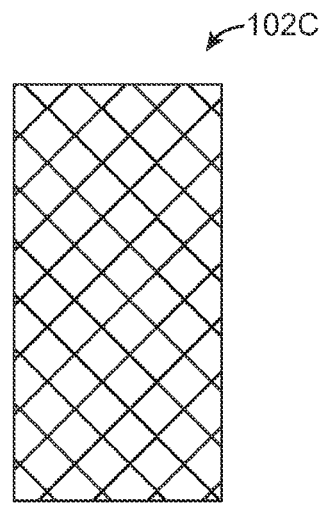
FIG. 1B          FIG. 1C
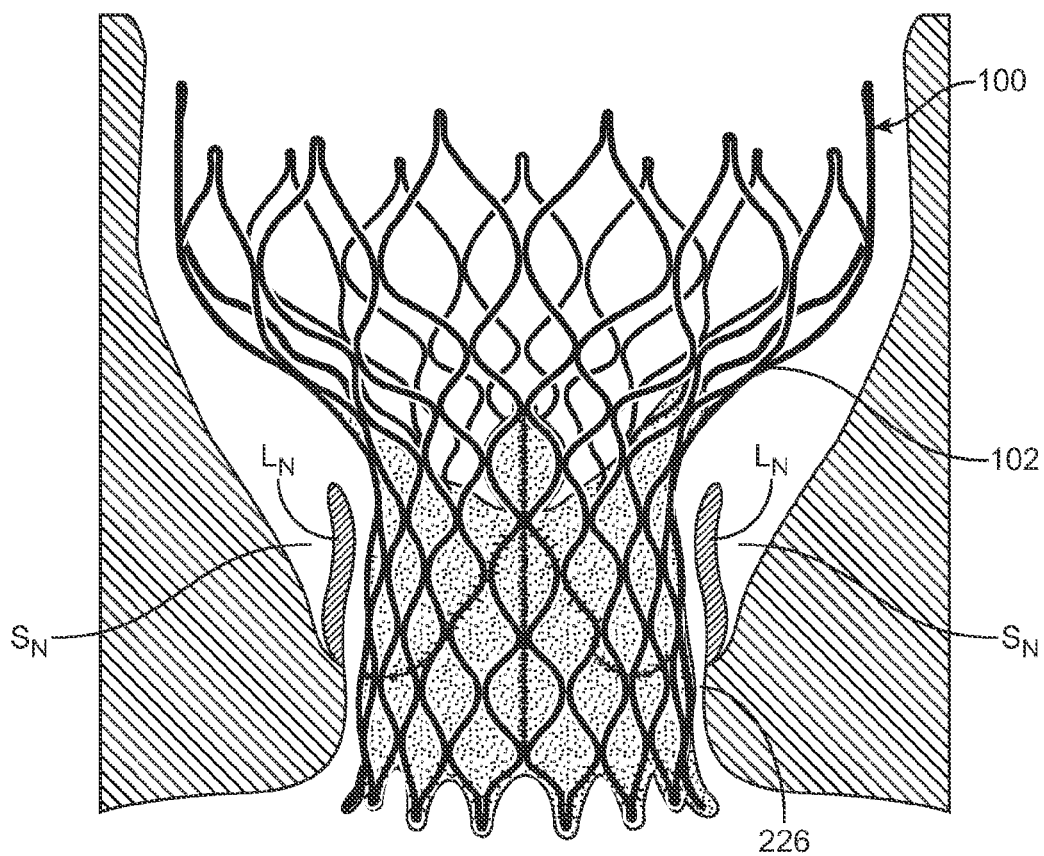
FIG. 2

ANTI-PARAVALVULAR LEAKAGE COMPONENTS FOR A TRANSCATHETER VALVE PROSTHESIS

FIELD OF THE INVENTION

The present invention relates to transcatheter valve prostheses and one or more anti-paravalvular leakage components formed on a surface of a transcatheter valve prosthesis for preventing paravalvular leakage.

BACKGROUND OF THE INVENTION

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Recently, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by crimping onto a balloon catheter or by being contained within a sheath component of a delivery catheter, and advanced through the venous or arterial vasculature. Once the prosthetic valve is positioned at the treatment site, for instance within an incompetent native valve, the stent structure may be expanded to hold the prosthetic valve firmly in place. One example of a stented prosthetic valve is disclosed in U.S. Pat. No. 5,957,949 to Leonhardt et al. entitled "Percutaneous Placement Valve Stent", which is incorporated by reference herein in its entirety. Another example of a stented prosthetic valve for a percutaneous pulmonary valve replacement procedure is described in U.S. Patent Application Publication No. 2003/0199971 A1 and U.S. Patent Application Publication No. 2003/0199963 A1, both filed by Tower et al., each of which is incorporated by reference herein in its entirety.

Although transcatheter delivery methods have provided safer and less invasive methods for replacing a defective native heart valve, leakage between the implanted prosthetic valve and the surrounding native tissue is a recurring problem. Leakage sometimes occurs due to the fact that minimally invasive and percutaneous replacement of cardiac valves typically does not involve actual physical removal of the diseased or injured heart valve. Rather, the replacement stented prosthetic valve is delivered in a compressed condition to the valve site, where it is expanded to its operational state within the mitral valve. Calcified or diseased native leaflets are pressed to the side walls of the native valve by the radial force of the stent frame of the prosthetic valve. These calcified leaflets do not allow complete conformance of the stent frame with the native valve and can be a source of paravalvular leakage (PVL). Significant pressure gradients across the valve cause blood to leak through the gaps between the implanted prosthetic valve and the calcified anatomy.

Embodiments hereof are related to anti-paravalvular leakage components coupled to the valve prosthesis to prevent paravalvular leakage.

BRIEF SUMMARY OF THE INVENTION

Embodiments hereof relate to a transcatheter valve prosthesis including a tubular stent having a compressed configuration for delivery within a vasculature and an expanded configuration for deployment within a native heart valve, a prosthetic valve component disposed within and secured to the stent, and an anti-paravalvular leakage component coupled to and encircling an outer surface of the tubular stent. The anti-paravalvular leakage component includes a skirt formed of a flexible material. The skirt has a first edge coupled to the tubular stent and an opposing second edge not coupled to the tubular stent. A radially expandable control ring is coupled to the second edge of the skirt. The control ring in an expanded diameter extends the second edge of the skirt outwardly away from the outer surface of the tubular stent and against the native heart valve to form an open-ended annular pocket between the skirt and the outer surface of the tubular stent.

According to another embodiment hereof, a transcatheter valve prosthesis includes a tubular stent having a compressed configuration for delivery within a vasculature and an expanded configuration for deployment within a native heart valve, a prosthetic valve component disposed within and secured to the stent, and an anti-paravalvular leakage component coupled to and encircling an outer surface of the tubular stent. The anti-paravalvular leakage component includes a skirt formed of a flexible material. The skirt has a first edge coupled to the tubular stent and an opposing second edge not coupled to the tubular stent. A control ring having an adjustable diameter is coupled to the second edge of the skirt. The diameter of the control ring may be varied in situ to selectively extend the second edge of the skirt outwardly away from the outer surface of the tubular stent and against the native heart valve.

According to another embodiment hereof, a transcatheter valve prosthesis includes a tubular stent having a compressed configuration for delivery within a vasculature and an expanded configuration for deployment within a native heart valve, a prosthetic valve component disposed within and secured to the stent, and an anti-paravalvular leakage component coupled to an inner surface of the tubular stent. The anti-paravalvular leakage component includes at least one flap formed of a flexible material moveable by blood flow. The flap has a first end coupled to the tubular stent adjacent to prosthetic valve component and an opposing second end not coupled to the tubular stent.

According to another embodiment hereof, a transcatheter valve prosthesis includes a tubular stent having a compressed configuration for delivery within a vasculature and an expanded configuration for deployment within a native heart valve, a prosthetic valve component disposed within and secured to the stent, and an anti-paravalvular leakage component coupled to and encircling an outer surface of the tubular stent. The anti-paravalvular leakage component includes a skirt formed of a flexible material. The skirt has first and second opposing edges coupled to the tubular stent to form one or more enclosed compartments between the skirt and the outer surface of the tubular stent. Each enclosed compartment includes a one-way valve which allows for blood flow into the compartment but prevents blood flow out of the compartment.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1B is a side view illustration of an alternative configuration of a heart valve prosthesis for use in embodiments hereof.

FIG. 1C is a side view illustration of an alternative configuration of a heart valve prosthesis for use in embodiments hereof.

FIG. 2 is a side view illustration of the heart valve prosthesis of FIG. 1 implanted within a native valve annulus.

DETAILED DESCRIPTION OF THE INVENTION

Specific embodiments of the present invention are now described with reference to the figures, wherein like reference numbers indicate identical or functionally similar elements. If utilized herein, the terms "distal" or "distally" refer to a position or in a direction away from the heart and the terms "proximal" and "proximally" refer to a position near or in a direction toward the heart. The following detailed description is merely exemplary in nature and is not intended to limit the invention or the application and uses of the invention. Although the description of the invention is in the context of treatment of heart valves, the invention may also be used where it is deemed useful in other valved intraluminal sites that are not in the heart. For example, the present invention may be applied to venous valves as well. Furthermore, there is no intention to be bound by any expressed or implied theory presented in the preceding technical field, background, brief summary or the following detailed description.

Figure 1:
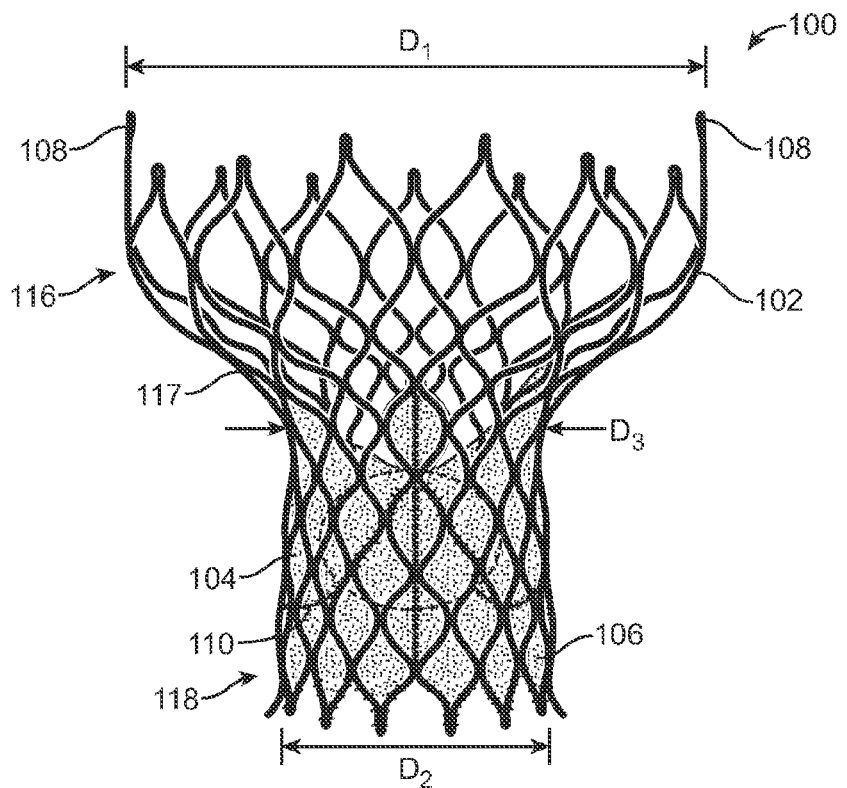
FIG. 1 is a side view illustration of an exemplary transcatheter heart valve prosthesis for use in embodiments hereof.

FIG. 1 depicts an exemplary transcatheter heart valve prosthesis 100. Heart valve prosthesis 100 is illustrated herein in order to facilitate description of the methods and devices to prevent and/or repair paravalvular leakage according to embodiments hereof. It is understood that any number of alternate heart valve prostheses can be used with the methods and devices described herein. Heart valve prosthesis 100 is merely exemplary and is described in more detail in U.S. Patent Application Pub. No. 2011/0172765 to Nguyen et al., which is herein incorporated by reference in its entirety.

Heart valve prosthesis 100 includes an expandable stent or frame 102 that supports a prosthetic valve component within the interior of stent 102. In embodiments hereof, stent 102 is self-expanding to return to an expanded deployed state from a compressed or constricted delivery state and may be made from stainless steel, a pseudo-elastic metal such as a nickel titanium alloy or Nitinol, or a so-called super alloy, which may have a base metal of nickel, cobalt, chromium, or other metal. "Self-expanding" as used herein means that a structure/component has a mechanical memory to return to the expanded or deployed configuration. Mechanical memory may be imparted to the wire or tubular structure that forms stent 102 by thermal treatment to achieve a spring temper in stainless steel, for example, or to set a shape memory in a susceptible metal alloy, such as nitinol, or a polymer, such as any of the polymers disclosed in U.S. Pat. Appl. Pub. No. 2004/0111111 to Lin, which is incorporated by reference herein in its entirety. Alternatively, heart valve prosthesis 100 may be balloon-expandable as would be understood by one of ordinary skill in the art.

Figure 1A:
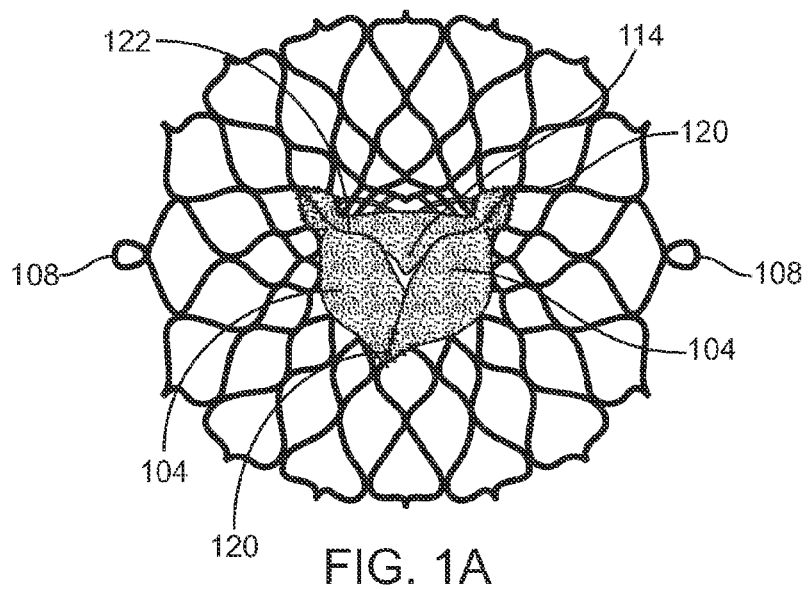
FIG. 1A is a top view illustration of the heart valve prosthesis of FIG. 1.

In the embodiment depicted in FIGS. 1 and 1A, stent 102 of valve prosthesis 100 has a deployed asymmetric hourglass configuration including an enlarged first end or section 116, a constriction or waist region 117, and a second end or section 118. Enlarged first section 116 has nominal deployed diameter $D_1$, second section 118 has nominal deployed diameter $D_2$, and constriction region 117 has deployed substantially fixed diameter $D_3$. Each section of stent 102 may be designed with a number of different configurations and sizes to meet the different requirements of the location in which it may be implanted. When configured as a replacement for an aortic valve, second section 118 functions as an inflow end of heart valve prosthesis 100 and extends into and anchors within the aortic annulus of a patient's left ventricle, while first section 116 functions as an outflow end of heart valve prosthesis 100 and is positioned in the patient's ascending aorta. When configured as a replacement for a mitral valve, enlarged first section 116 functions as an inflow end of heart valve prosthesis 100 and is positioned in the patient's left atrium, while second section 118 functions as an outflow end of heart valve prosthesis 100 and extends into and anchors within the mitral annulus of a patient's left ventricle. For example, U.S. Patent Application Publication Nos. 2012/0101572 to Kovalsky et al. and 2012/0035722 to Tuval, each of which are herein incorporated by reference in their entirety, illustrate heart valve prostheses configured for placement in a mitral valve. Each section of stent 102 may have the same or different cross-section which may be for example circular, ellipsoidal, rectangular, hexagonal, rectangular, square, or other polygonal shape, although at present it is believed that circular or ellipsoidal may be preferable when the valve prosthesis is being provided for replacement of the aortic or mitral valve. As alternatives to the deployed configuration of FIGS. 1 and 1A, the stent/valve support frame may have an hourglass configuration 102B shown in FIG. 1B, a generally tubular configuration 102C as shown in FIG. 1C, or other stent configuration or shape known in the art for valve replacement. Stent 102 also may include eyelets 108 that extend from first end 116 thereof for use in loading the heart valve prosthesis 100 into a delivery catheter (not shown).

As previously mentioned, heart valve prosthesis 100 includes a prosthetic valve component within the interior of stent 102. The prosthetic valve component is capable of blocking flow in one direction to regulate flow there through via valve leaflets 104 that may form a bicuspid or tricuspid replacement valve. FIG. 1A is an end view of FIG. 1 and illustrates an exemplary tricuspid valve having three leaflets 104, although a bicuspid leaflet configuration may alternatively be used in embodiments hereof. More particularly, if heart valve prosthesis 100 is configured for placement within a native valve having three leaflets such as the aortic, tricuspid, or pulmonary valves, heart valve prosthesis 100 includes three valve leaflets 104. If heart valve prosthesis 100 is configured for placement within a native valve having two leaflets such as the mitral valve, heart valve prosthesis 100 includes two valve leaflets 104. Valve leaflets 104 are sutured or otherwise securely and sealingly attached to the interior surface of stent 102 and/or graft material 106 which encloses or lines a portion of stent 102 as would be known to one of ordinary skill in the art of prosthetic tissue valve construction. Referring to FIG. 1, leaflets 104 are attached along their bases 110 to graft material 106, for example, using sutures or a suitable biocompatible adhesive. Adjoining pairs of leaflets are attached to one another at their lateral ends to form commissures 120, with free edges 122 of the leaflets forming coaptation edges that meet in area of coaptation 114.

Leaflets 104 may be made of pericardial material; however, the leaflets may instead be made of another material. Natural tissue for replacement valve leaflets may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as leaflets 104 include DACRON® polyester commercially available from Invista North America S.A.R.L. of Wilmington, Del., other cloth materials, nylon blends, polymeric materials, and vacuum deposition nitinol fabricated materials. One polymeric material from which the leaflets can be made is an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

Graft material 106 may also be a natural or biological material such as pericardium or another membranous tissue such as intestinal submucosa. Alternatively, graft material 106 may be a low-porosity woven fabric, such as polyester, Dacron fabric, or PTFE, which creates a one-way fluid passage when attached to the stent. In one embodiment, graft material 106 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. In one embodiment shown in FIG. 1, graft material 106 extends from leaflets bases 110 to second end 118 of heart valve prosthesis.

Delivery of heart valve prosthesis 100 may be accomplished via a percutaneous transfemoral approach or a transapical approach directly through the apex of the heart via a thoracotomy, or may be positioned within the desired area of the heart via different delivery methods known in the art for accessing heart valves. During delivery, if self-expanding, the prosthetic valve remains compressed until it reaches a target diseased native heart valve, at which time the heart valve prosthesis 100 can be released from the delivery catheter and expanded in situ via self-expansion. The delivery catheter is then removed and heart valve prosthesis 100 remains deployed within the native target heart valve. Alternatively, heart valve prosthesis 100 may be balloon-expandable and delivery thereof may be accomplished via a balloon catheter as would be understood by one of ordinary skill in the art.

FIG. 2 is a side view illustration of heart valve prosthesis 100 implanted within a native aortic heart valve, which is shown in section, having native leaflets $L_N$ and corresponding native sinuses $S_N$. When heart valve prosthesis 100 is deployed within the valve annulus of a native heart valve, stent 102 expands within native valve leaflets $L_N$ of the patient's defective valve, retaining the native valve leaflets in a permanently open state. The native valve annulus may include surface irregularities on the inner surface thereof, and as a result one or more gaps or cavities/crevices 226 may be present or may form between the perimeter of heart valve prosthesis 100 and the native valve annulus. For example, calcium deposits may be present on the native valve leaflets (e.g., stenotic valve leaflets) and/or shape differences may be present between the native heart valve annulus and prosthesis 100. More particularly, in some cases native annuli are not perfectly rounded and have indentations corresponding to the commissural points of the native valve leaflets. As a result, a prosthesis having an approximately circular shape does not provide an exact fit in a native valve. These surface irregularities, whatever their underlying cause, can make it difficult for conventional prosthetic valves to form a blood tight seal between the prosthetic valve and the inner surface of the valve annulus, causing undesirable paravalvular leakage and/or regurgitation at the implantation site.

Embodiments hereof relate to methods for delivering a heart valve prosthesis having a anti-paravalvular leakage component coupled to and encircling an outer surface of the heart valve prosthesis in order to occlude or fill gaps between the perimeter of a heart valve prosthesis and the native valve annulus, thereby reducing, minimizing, or eliminating leaks there through. More particularly, with reference to FIG. 3 and FIG. 4, an anti-paravalvular leakage component 330 includes a skirt 332 formed of a flexible material and a radially expandable control ring 334. Skirt 332 is a flap having has a first end or edge coupled to stent 102 and an opposing second end or edge not coupled to stent 102. As used herein, a flap is a moveable piece of flexible material that has at least a portion of the first edge attached to stent 102. The first end or edge of skirt 332 may be attached to stent 102 by any suitable means known to those skilled in the art, for example and not by way of limitation, welding, adhesive, suture, or mechanical coupling. As will be explained in more detail herein, expandable control ring 334 is coupled to the second or unattached edge of skirt 332 and operates to radially extend or deploy the unattached edge of skirt 332 outwardly away from stent 102 to form an open-ended annular pocket or compartment 336 between an inner surface of the skirt and the outer surface of the tubular stent. Open-ended pocket 336 catches and blocks any retrograde flow within the native valve, thereby preventing undesired regurgitation and preventing blood stagnation in and around the native valve sinuses. In addition, when deployed, anti-paravalvular leakage component 330 radially expands into and substantially fills any/all gaps or cavities/crevices between outer surface 103 of stent 102 and native valve tissue. "Substantially" as utilized herein means that blood flow through the target gap or cavity is occluded or blocked, or stated another way blood is not permitted to flow there through. Anti-paravalvular leakage component 330 functions as a continuous circumferential seal around heart valve prosthesis 100 to block or prevent blood flow around the outer perimeter of the prosthesis, thereby minimizing and/or eliminating any paravalvular leakage at the implantation site.

Although embodiments depicted herein illustrate open-ended annular pocket 336 of anti-paravalvular leakage component 330 oriented to catch retrograde blood flow, it would be obvious to one of ordinary skill in the art that pocket 336 may be inverted to catch antegrade flow rather than retrograde flow. More particularly, open-ended annular pocket 336 can be oriented in the opposite direction (i.e., to prevent forward blood flow), with its open side facing generally towards second end 118 of heart valve prosthesis rather than facing generally towards first end 116 of heart valve prosthesis.

Figure 3:
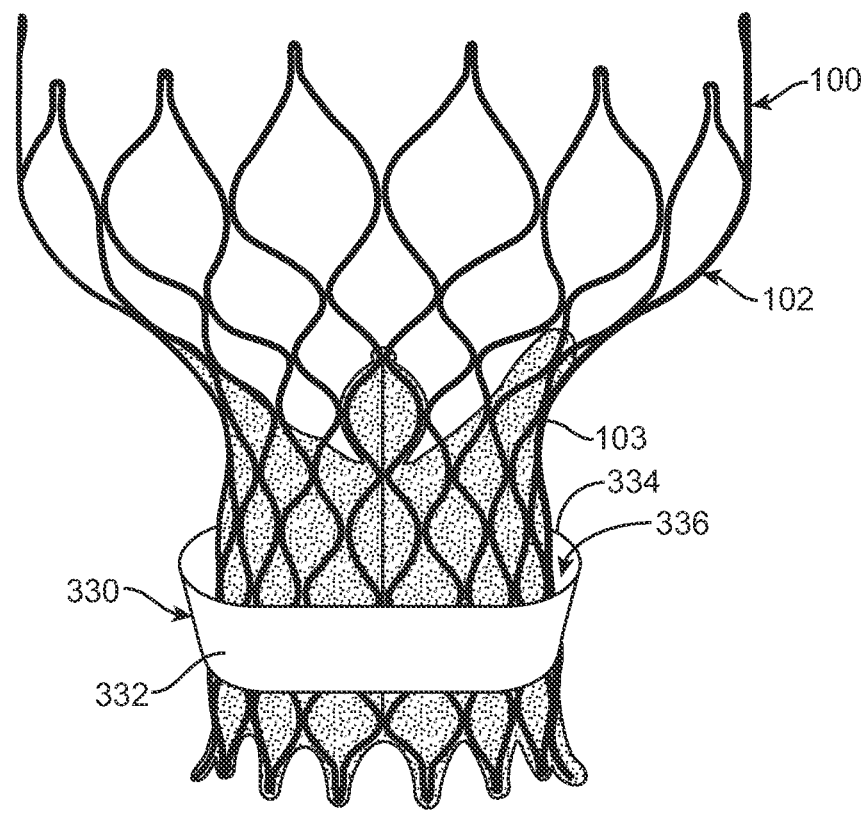
FIG. 3 is a side view illustration of a heart valve prosthesis including an anti-paravalvular leakage component around an outer surface thereof, wherein the anti-paravalvular leakage component includes a skirt and a radially expandable control ring.
Figure 4:
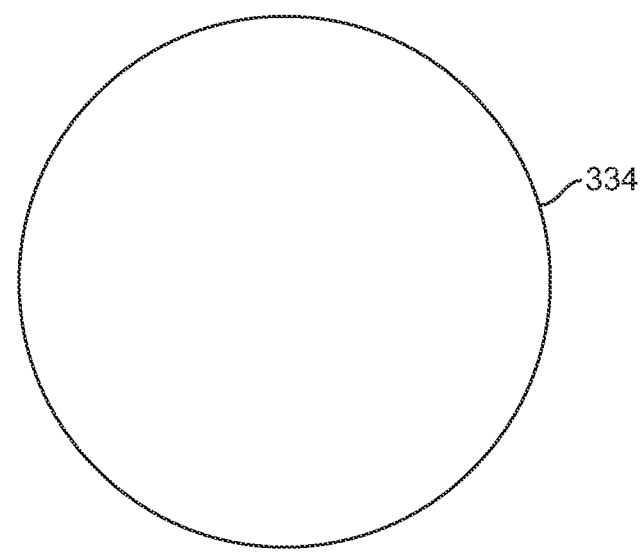
FIG. 4 is a top view of the control ring of FIG. 3, removed from the heart valve prosthesis for illustration purposes only.

In the embodiment of FIGS. 3-4, anti-paravalvular leakage component 330 is coupled to outer surface 103 of heart valve prosthesis 100 along constriction region 117 thereof, described with respect to FIG. 1 above. When deployed, anti-paravalvular leakage component 330 may be positioned in situ at the native valve annulus, slightly above the valve annulus, slightly below the valve annulus, or some combination thereof. Since the annular anti-paravalvular leakage component is coupled to outer surface 103 of heart valve prosthesis 100, longitudinal placement and/or the size and shape thereof is flexible and may be adjusted or adapted according to each application and to a patient's unique needs. For example, depending on the anatomy of the particular patient, the anti-paravalvular leakage component may be positioned on heart valve prosthesis 100 so that in situ the anti-paravalvular leakage component is positioned between heart valve prosthesis 100 and the interior surfaces of the native valve leaflets, between heart valve prosthesis 100 and the interior surfaces of the native valve annulus, and/or between heart valve prosthesis 100 and the interior surfaces of the left ventricular outflow track (LVOT).

Suitable materials for skirt 332 include but are not limited to a low-porosity woven fabric such as polyester, Dacron fabric, or PTFE. Porous materials advantageously provide a medium for tissue ingrowth. Further, skirt 332 may be pericardial tissue or may be a knit or woven polyester, such as a polyester or polytetrafluoroethylene (PTFE) knit, both of which provide a medium for tissue ingrowth and have the ability to stretch to conform to a curved surface. Polyester velour fabrics may alternatively be used, such as when it is desired to provide a medium for tissue ingrowth on one side and a smooth surface on the other side. Elastomeric materials such as but not limited to polyurethane may also be used as a material for skirt 332.

Figure 5A:
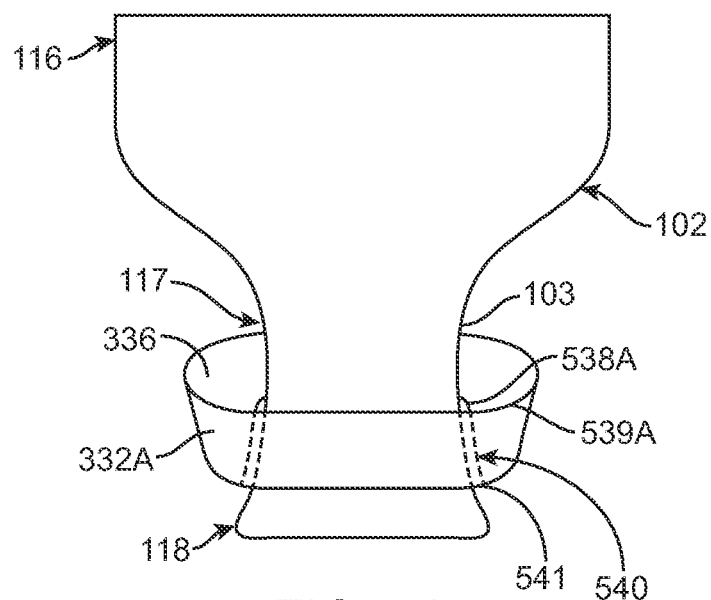
FIG. 5A is a side view illustration of the heart valve prosthesis of FIG. 3, wherein the skirt includes a folded double layer.

Skirt 332 may include an integral folded portion which essentially creates two layers or a double layer of fabric that extends over a portion of the outer surface of stent 102. More particularly, as shown in the embodiment of FIG. 5A, a first edge 538A of skirt 332A is attached or coupled to outer surface 103 of stent 102 along constriction region 117 thereof, described with respect to FIG. 1 above. A portion 540 of skirt 332A abuts against outer surface 103 of stent 102 and extends over stent 102 in a direction towards second end 118, creating an inner layer of skirt material. In an embodiment, portion 540 may be attached to stent 102 by any suitable means known to those skilled in the art, for example and not by way of limitation, welding, adhesive, suture, or mechanical coupling. In another embodiment, portion 540 may be unattached to stent 102. Skirt 332A includes an integral fold 541 in the skirt material such that the remainder of skirt 332A bends over itself and extends in a direction towards first end 116, thereby creating an outer layer of skirt material that extends over stent 102. Fold 541 may be attached to stent 102 or may be unattached to stent 102. A second edge 539A of skirt 332B is unattached to stent 102 and coupled to control ring 334 (not shown in FIG. 5A) so that when control ring 334/second edge 539A is radially extended, the outer layer of skirt material is spaced apart from outer surface 103 of stent 102 and open-ended annular pocket 336 is formed between the inner and outer layers of skirt material.

Figure 5B:
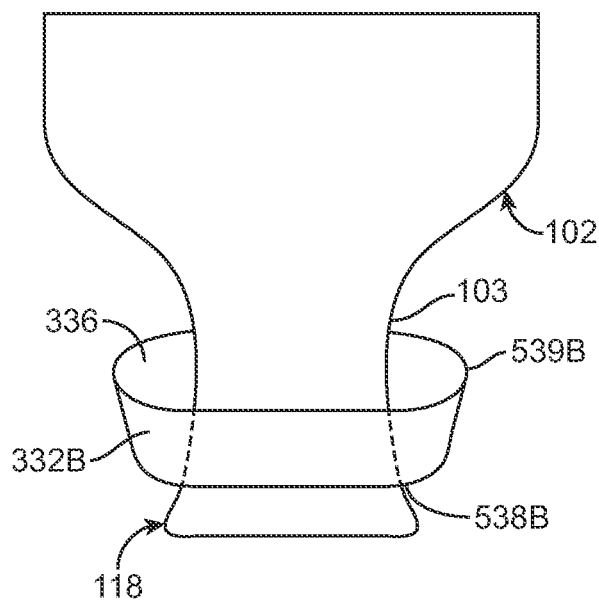
FIG. 5B is a side view illustration of the heart valve prosthesis of FIG. 3, wherein the skirt includes a single layer.

In another embodiment hereof, skirt 332 may include only a single layer of fabric that extends over a portion of the outer surface of stent 102. More particularly, as shown in the embodiment of FIG. 5B, a first edge 538B of skirt 332B is attached or coupled to outer surface 103 of stent 102 adjacent to second end 118 thereof. Skirt 332A extends in a direction towards first end 116 of stent 102. A second edge 539B of skirt 332B is unattached to stent 102 and coupled to control ring 334 (not shown in FIG. 5B) so that when control ring 334/second edge 539B is radially extended, the single layer skirt 332B is spaced apart from outer surface 103 of stent 102 and open-ended annular pocket 336 is formed between skirt 332 and stent 102.

Figure 6A:
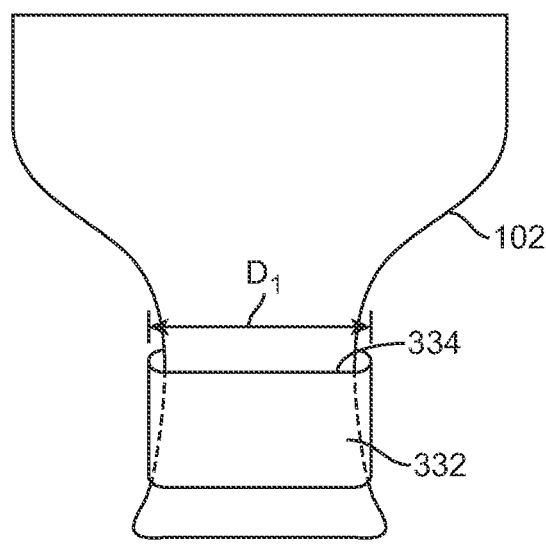
FIG. 6A is a side view illustration of the heart valve prosthesis of FIG. 3, wherein the control ring is self-expanding and in a first non-expanded configuration.
Figure 6B:
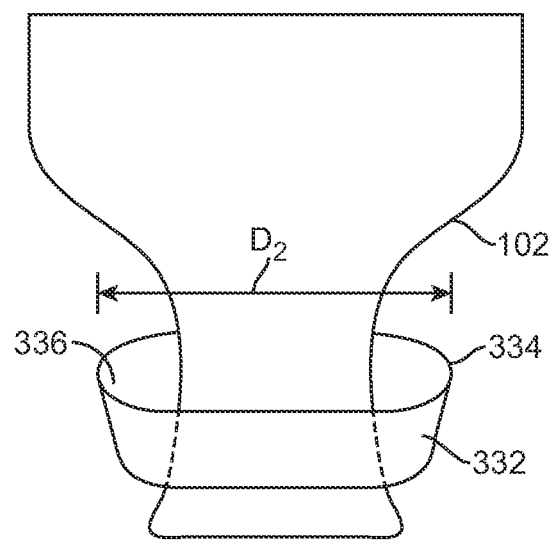
FIG. 6B is a side view illustration of the heart valve prosthesis of FIG. 3, wherein the control ring is self-expanding and in an second expanded configuration.

With additional reference to FIGS. 6A and 6B, ring 334 operates in situ to radially expand or extend free or unattached second edge of skirt 332 outwardly away from valve prosthesis and thereby form open-ended annular pocket 336. As shown in FIG. 6A, in a first configuration, ring 334 has a first diameter $D_1$ which is approximately equal to an expanded diameter of heart valve prosthesis 100. Ring 334 expands to a second diameter $D_2$, which is larger than first diameter $D_1$, during or after deployment of heart valve prosthesis 100 as shown in FIG. 6B. Second diameter $D_2$ is greater than an expanded diameter of heart valve prosthesis 100 so that when ring 334 expands to second diameter $D_2$, it radially extends the second unattached edge of skirt 332 outwardly away from the outer surface of the heart valve prosthesis and forms open-ended annular pocket 336.

In an embodiment, ring 334 is formed from a self-expanding material that returns to an expanded deployed state in which the diameter of ring 334 is second diameter $D_2$ from a compressed or constricted delivery state. The diameter of ring 334 in the compressed or constricted delivery state is approximately equal to the compressed or constricted delivery diameter of stent 102. "Self-expanding" as used herein means that a structure/component has a mechanical memory to return to the expanded or deployed configuration. Mechanical memory may be imparted to the wire or tubular structure that forms ring 334 by thermal treatment to achieve a spring temper in stainless steel, for example, or to set a shape memory in a susceptible metal alloy, such as nitinol, or a polymer. Accordingly, ring 334 may be made from stainless steel, a pseudo-elastic metal such as a nickel titanium alloy or Nitinol, or a so-called super alloy, which may have a base metal of nickel, cobalt, chromium, or other metal.

Figure 7:
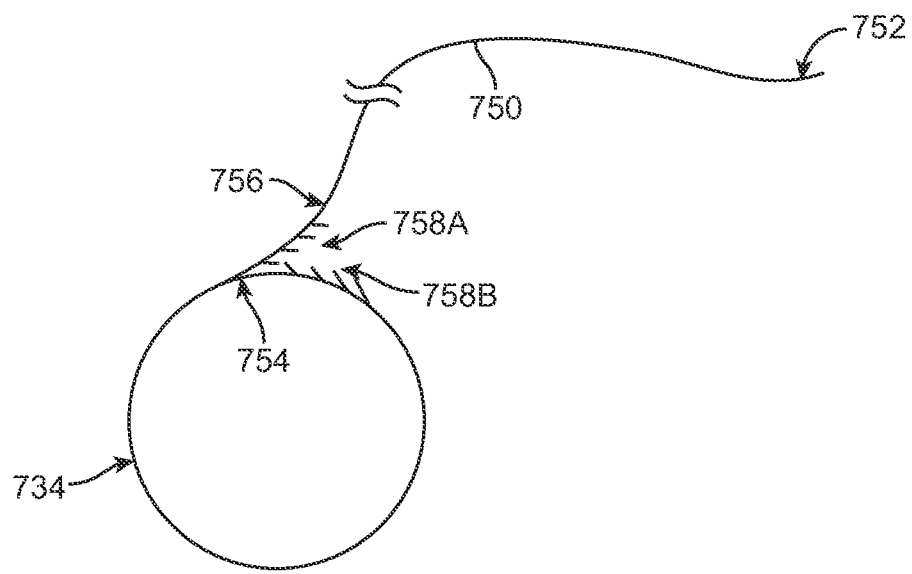
FIG. 7 is a top view illustration of an elongated strand that forms a control ring for use with the anti-paravalvular leakage component of FIG. 3, wherein a diameter of the control ring is adjustable in situ via a series of interlocking teeth.
Figure 8:
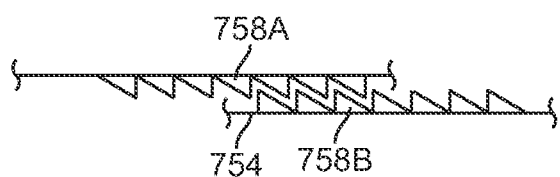
FIG. 8 is an enlarged side view of the series of interlocking teeth of FIG. 7.

In another embodiment hereof, the control ring has an adjustable diameter that may be varied in situ to selectively extend the second unattached edge of skirt 332 outwardly away from the outer surface of the heart valve prosthesis. For example, FIGS. 7 and 8 illustrate an embodiment of a control ring 734 having an adjustable diameter that may be varied in situ. More particularly, an elongated strand 750 has a first end 752 and a second end 754. Elongated strand 750 extends through a lumen of a delivery system (not shown) such that first end 752 of elongated strand 750 extends to a position outside of the body. Second end 754 of elongated strand 750 is slidingly positioned over a body of strand 750 via a series of interlocking teeth 758A, 758B and forms or divides strand 750 into control ring 734 and a tether or remainder 756. As shown in the enlarged view of FIG. 8, teeth 758A are formed on a first surface of strand 750 and teeth 758B are formed on a second surface of strand 750 that abuts against the first surface when a portion of strand 750 is formed or shaped into control ring 734. Teeth 758A, 758B mate or interlock together in a male/female relationship. First end 752 of strand 750 is pushed or pulled to ratchet or move teeth 758A forward or backward, respectively, over teeth 758B and thereby expand or contract the diameter of control ring 734.

Figure 9A:
FIGS. 9A-9C are side views of a weakened area which is formed on the elongated strand of FIG. 7 according to embodiments hereof.
Figure 9B:
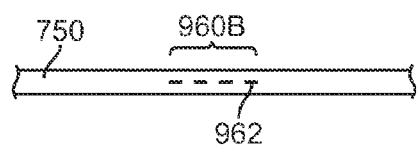
Figure 9C:
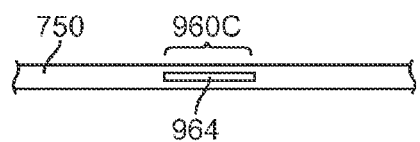

Strand 750 includes at least one weakened area or break point that breaks or splits apart when force is applied thereto. The weakened area may be of various constructions as illustrated in FIGS. 5A-5F. In FIG. 9A, a weakened area 960A is formed via a short segment of strand 750 having a smaller diameter than the remaining length of strand 750. In FIG. 9B, a weakened area 960B is formed via a perforations or serrations 962. Perforations or serrations 962 include a series of holes in the form of one or more lines provided by perforating a short segment of strand 750. Although a straight line of perforations 962 is shown in FIG. 9B, a wavy or zig-zag pattern of perforations may be utilized without departing from the scope of the present invention. In addition, although perforations 962 are shown as a series of longitudinal lines it would be understood by those of ordinary skill in the art that the lines may additionally and/or alternatively made in the radial direction. A weakened area 960C may also include a slit, slot, or groove 964 as illustrated in FIG. 9C. Slit or slot 964 includes a straight cut, opening, or aperture in the form of one or more longitudinal lines provided by scoring or cutting strand 750. Slit, slot, or groove 964 has a width that may be greater or equal to zero. In other words, slit, slot, or groove 964 may include a cut with approximately zero width or may include an opening or aperture with a narrow width. Slit, slot, or groove 964 may have a depth that extends from the inside surface to the outside surface of strand 750, or alternatively may have a depth that extends only partially within the material of strand 750.

Figures 10A, 10B:
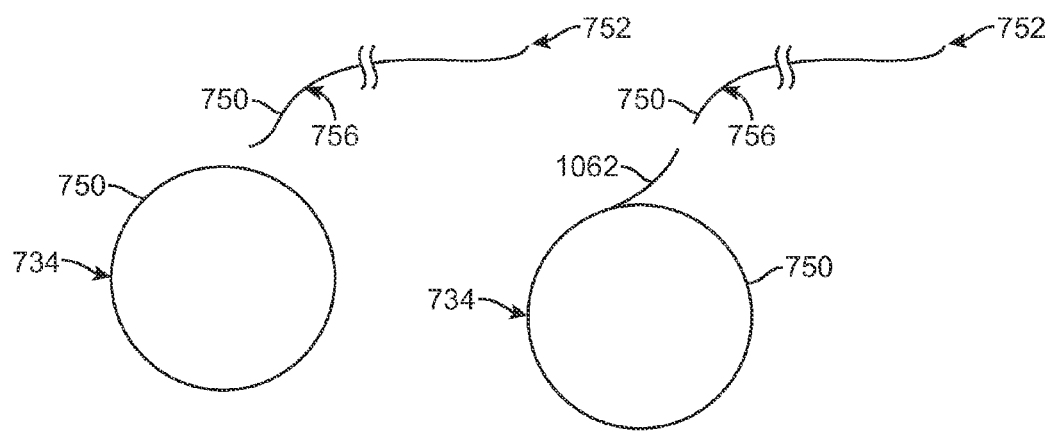
FIGS. 10A and 10B are top view illustrations of the elongated strand of FIG. 7, wherein the strand has been segmented or divided via a weakened area according to embodiments hereof.

Once the control ring is expanded to the desired diameter in situ, control ring 734 is disconnected from tether or remainder 756 via user-applied force that breaks or splits the weakened area apart. The user-applied force require to break the weakened area of strand 750 may include but not is not limited to twisting strand 750, applying tension to strand 750, and/or utilizing an external mechanism to pinch the weakened area of strand 750. In one embodiment, strand 750 includes a plurality of weakened areas located between adjacent or abutting teeth 758A (not shown on FIGS. 10A and 10B). When a user applies the required force to break apart a weakened area of strand 750, control ring 734 is disconnected from tether or remainder 756 at the weakened area closest or nearest to the user which is not interlocked with teeth 758B (not shown on FIGS. 10A and 10B). As such, as depicted in FIG. 10A, tether 756 may be removed from the patient and only control ring 734 remains in situ. In another embodiment depicted in FIG. 10B, strand 750 includes a single weakened area that is spaced apart from teeth 758A (not shown on FIGS. 10A and 10B), located towards first end 752. When a user applies the required force to break apart the weakened area of strand 750, control ring 734 is disconnected from tether or remainder 756 at the weakened area and a relatively short tail or segment 1062 of strand 750 extending from control ring 734 remains in situ after tether 756 is removed from the patient.

Figure 11:
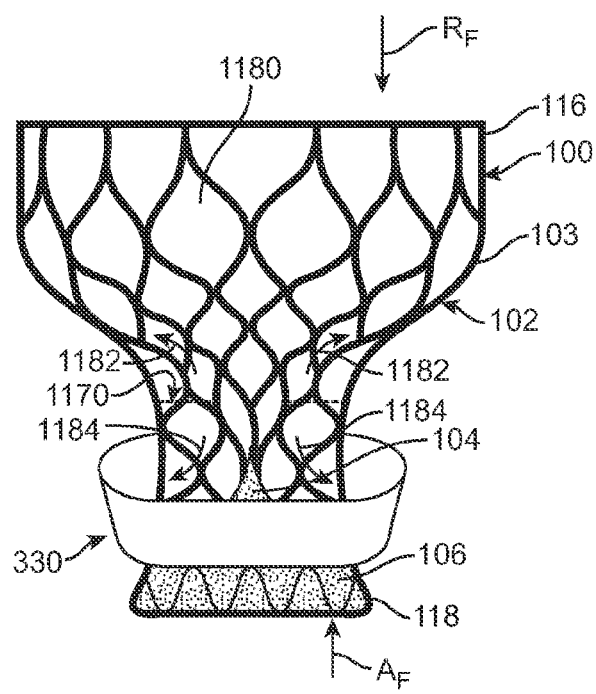
FIG. 11 is a side view illustration of a heart valve prosthesis including a first anti-paravalvular leakage component around an outer surface thereof and a second anti-paravalvular leakage component coupled to an inner surface thereof.
Figure 12A:
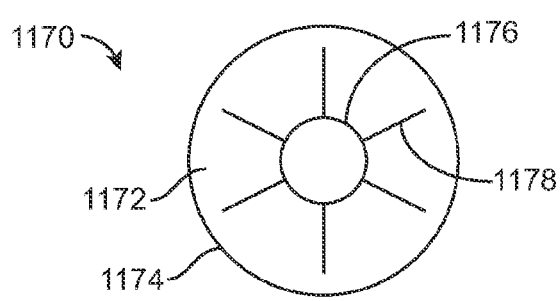
FIGS. 12A and 12B are top view illustrations of embodiments of the second anti-paravalvular leakage component of FIG. 11, removed from the heart valve prosthesis for illustration purposes only.
Figure 12B:
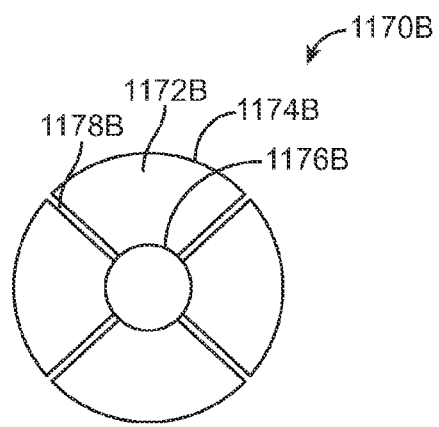

In addition or as an alternative to an anti-paravalvular leakage component which extends around the perimeter of a heart valve prosthesis to prevent paravalvular leakage, a heart valve prosthesis may include an anti-paravalvular leakage component coupled to an inner surface of the heart valve prosthesis. More particularly, with reference to FIG. 11, heart valve prosthesis 100 is shown with a first anti-paravalvular leakage component 330 around the perimeter thereof and a second anti-paravalvular leakage component 1170 coupled to an inner surface thereof. Second anti-paravalvular leakage component 1170 includes a flap 1172 having has a first end or edge 1174 coupled to stent 102 and an opposing second end or edge 1176 not coupled to stent 102. As used herein, a flap is a moveable piece of flexible material that has at least a portion of the first edge attached to stent 102. The first end or edge of flap 1172 may be attached to stent 102 by any suitable means known to those skilled in the art, for example and not by way of limitation, sutures or a suitable biocompatible adhesive. In one embodiment depicted in FIG. 12A, flap 1172 is annular or donut-shaped and includes a plurality of radially-extending slits 1178 extending from second edge 1176 thereof. In another embodiment hereof, shown in FIG. 12B, anti-paravalvular leakage component 1170B includes a plurality of adjacent flaps 1172B each having a first end or edge 1174B to be coupled to stent 102 (not shown in FIG. 12B) and an opposing second end or edge 1176B which is not coupled to stent 102. Flaps 1172B are oriented around the inner surface of the stent such that a relatively small gap or space 1178B extends between adjacent pairs of flaps 1172B. Although FIG. 12B illustrates anti-paravalvular leakage component 1170B with four flaps 1172B, it will be understood by one of ordinary skill in the art that four flaps is exemplary and a greater or lesser number of flaps may be utilized.

Flap 1172 is moveable by blood flow, i.e., in situ the flap is displaced in the direction of blood flow, and operates to cover open spaces 1180 of within tubular stent 102 which are not covered by graft material 106 in order to prevent blood flow from leaking through valve prosthesis 100. More particularly, as described with respect to FIG. 1, in one embodiment hereof graft material 106 extends from the bases of leaflets 104 to second end 118 of heart valve prosthesis 100 but does not extend from the bases of leaflets 104 to first end 116. Accordingly, in FIG. 1, blood may flow through or within the open spaces of stent 102. However, in the embodiment of FIG. 11, flap 1172 is located above leaflets 104, closer to first end 116 of heart valve prosthesis 100. Due to antegrade blood flow represented by arrow $A_F$ through heart valve prosthesis 100, flap 1172 moves in a first direction indicated by directional arrow 1182 and is pressed against the inner surface of stent 102 to cover adjacent open spaces 1180 thereof. Similarly, due to retrograde blood flow represented by arrow $R_F$ through heart valve prosthesis 100, flap 1172 moves in a second opposing direction indicated by directional arrow 1184 and is pressed against the inner surface of stent 102 to cover adjacent open spaces 1180 thereof. By covering opening spaces 1180, blood flow is prevented or substantially reduced from flowing from inside heart valve prosthesis into any/all gaps or cavities/crevices between outer surface 103 of stent 102 and native valve tissue, thereby minimizing and/or eliminating any paravalvular leakage at the implantation site.

Suitable materials for flap 1172 include but are not limited to a low-porosity woven fabric, such as polyester, Dacron fabric, or PTFE. Porous materials advantageously provide a medium for tissue ingrowth. Further, flap 1172 may be pericardial tissue or may be a knit or woven polyester, such as a polyester or polytetrafluoroethylene (PTFE) knit, both of which have the ability to stretch to conform to a curved surface.

Figure 13:
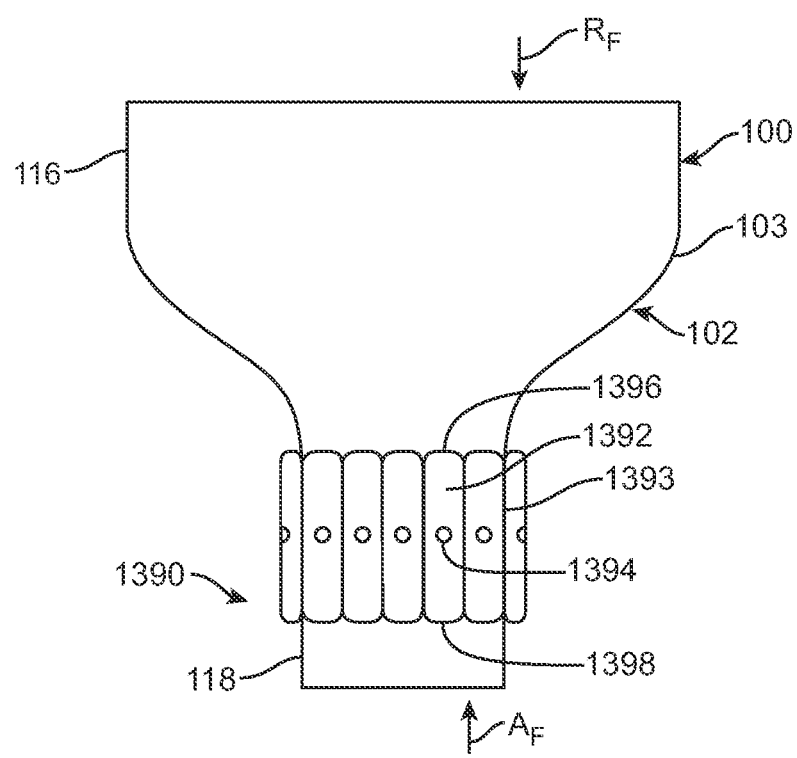
FIG. 13 is a side view illustration of a heart valve prosthesis including an anti-paravalvular leakage component around an outer surface thereof, wherein the anti-paravalvular leakage component includes a skirt that forms a plurality of enclosed compartments around the heart valve prosthesis.

FIG. 13 illustrates another embodiment hereof in which an anti-paravalvular leakage component is coupled to and encircles an outer surface of a heart valve prosthesis in order to occlude or fill gaps between the perimeter of a heart valve prosthesis and the native valve annulus, thereby reducing, minimizing, or eliminating leaks there through. More particularly, an anti-paravalvular leakage component 1390 includes a skirt 1392 formed of a flexible material that has first and second opposing edges 1396, 1398 coupled to stent 102 to form one or more enclosed pockets or compartments between skirt 1392 and outer surface 103 of stent 102. Stated another way, the enclosed pockets or compartments are closed or sealed via first and second opposing edges 1396, 1398 of skirt being coupled to stent 102. Edges 1396, 1398 of skirt 1392 may be attached to stent 102 by any suitable means known to those skilled in the art, for example and not by way of limitation, welding, adhesive, suture, or mechanical coupling. As shown in FIG. 13, a plurality of dividers or seams 1393 may be provided on skirt 1392 to form a plurality of compartments positioned around stent 102. The compartments can be formed in any number, size, and/or shape around stent 102. Suitable materials for skirt 1392 include but are not limited to a low-porosity woven fabric, such as polyester, Dacron fabric, or PTFE. Porous materials advantageously provide a medium for tissue ingrowth. Further, skirt 1392 may be pericardial tissue or may be a knit or woven polyester, such as a polyester or polytetrafluoroethylene (PTFE) knit, both of which provide a medium for tissue ingrowth and have the ability to stretch to conform to a curved surface. Polyester velour fabrics may alternatively be used, such as when it is desired to provide a medium for tissue ingrowth on one side and a smooth surface on the other side.

Each pocket or compartment includes a one-way port or valve 1394 which allows for blood flow into the pocket but prevents blood flow out of the pocket. Examples of valve 1394 are described in more detail herein with respect to FIG. 14 and FIGS. 15-16. In situ, blood flow between the perimeter of heart valve prosthesis 100 and the native valve annulus fills each pocket or compartment with blood. As each pocket or compartment fills with blood, skirt 1392 (which forms the outer surface of the pocket or compartment) radially or outwardly expands into and substantially fills any/all gaps or cavities/crevices between outer surface 103 of stent 102 and native valve tissue. "Substantially" as utilized herein means that blood flow through the target gap or cavity is occluded or blocked, or stated another way blood is not permitted to flow there through. Blood is essentially trapped within each pocket in order to prevent blood stagnation and form a seal. Anti-paravalvular leakage component 1390 functions as a seal for heart valve prosthesis 100 to block or prevent blood flow around the outer perimeter of the prosthesis, thereby minimizing and/or eliminating any paravalvular leakage at the implantation site.

Figure 14:
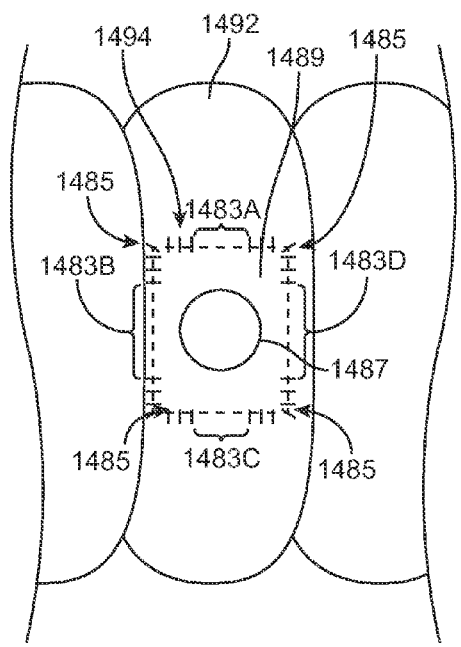
FIG. 14 is a side view of an embodiment of a valve used with the anti-paravalvular leakage component of FIG. 13.

In one embodiment shown in FIG. 14, the one-way port or valve is a membrane which allows flow in one direction therethrough. More particularly, FIG. 14 illustrates a valve 1494 coupled to a skirt 1492. Valve 1494 includes a membrane or segment of material 1489 which is coupled to an inside surface of skirt 1492 and extends over a hole or opening 1487 formed through the skirt. Membrane 1489 may be generally rectangular and formed from an elastic material or a fabric material such as Goretex or Musto. Membrane 1489 is coupled to skirt 1492 via a plurality of stitches 1485, which couple only the corners of the membrane to the skirt while unstitched segments 1483A, 1483B, 1483C, 1483D of membrane 1489 between the stitches are not coupled to skirt 1492. Under no pressure or in a default state, valve 1494 is in a closed or sealed configuration in which membrane 1489 lies flat and sealingly against opening 1478. In operation, in situ, blood pressure deforms valve 1494 into an open configuration. More particularly, blood flows through opening 1487 and the pressure of the blood deforms or deflects membrane 1489 to create channels via unstitched segments 1483A, 1483B, 1483C, 1483D of membrane 1489. In the open configuration, blood is permitted to flow into each pocket or compartment formed by skirt 1492 through channels which are created at the unstitched segments between the inner surface of skirt 1492 and the outer surface of membrane 1489. Once the pressure drops, membrane 1489 returns to the closed configuration in which membrane 1489 lies flat against and covers opening 1478, thereby trapping blood within each pocket to form a seal around the outer perimeter of the prosthesis.

Figure 15:
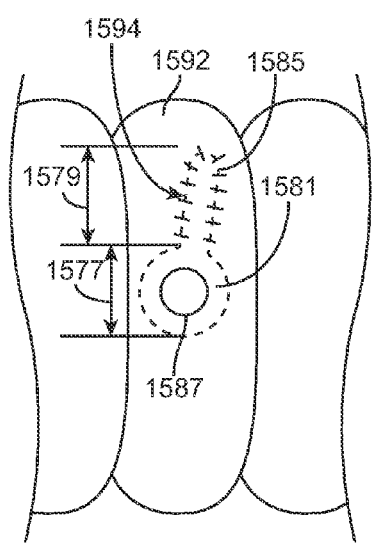
FIG. 15 is a side view of another embodiment of a valve used with the anti-paravalvular leakage component of FIG. 13.
Figure 16:
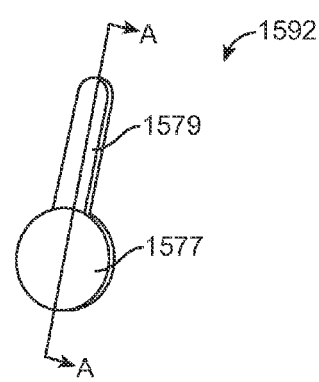
FIG. 16 is a perspective view of the valve of FIG. 15, wherein the valve is removed from the anti-paravalvular leakage component for purposes of illustration only.
Figure 16A:
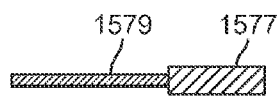
FIG. 16A is a cross-sectional view taken along line A-A of FIG. 16.
Figure 16B:
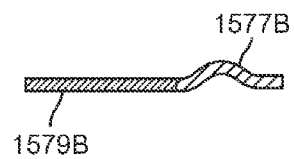
FIG. 16B is a cross-sectional view taken along line A-A of FIG. 16 according to an alternate embodiment.

In another embodiment shown in FIGS. 15, 16, 16A, and 16B, the one-way port or valve is a flap valve which allows flow in one direction therethrough. More particularly, FIG. 15 illustrates a valve 1594 coupled to a skirt 1592 while FIG. 16 illustrates valve 1594 removed from the prosthesis for illustration purposes only. Valve 1594 includes is a membrane or segment of material 1581 that has a paddle configuration with a stem or handle portion 1579 coupled to an inside surface of skirt 1592 via a plurality of stitches 1585 and a flap portion 1577, which is not coupled to skirt 1592. Membrane 1581 may be formed from a polymer material. Under no pressure or in a default state, valve 1594 is in a closed or sealed configuration in which flap portion 1577 of membrane 1581 extends over or covers opening 1587 formed through skirt 1592. As shown in FIG. 16A, flap portion 1577 may be generally straight such that it lies flat and extends over opening 1587 in the closed configuration. In another configuration shown in FIG. 16B, flap portion 1577 may be curved such that it protrudes into and/or through opening 1587 in the closed configuration. In operation, in situ, blood pressure deforms valve 1594 into an open configuration. More particularly, blood flows through opening 1587 and the pressure of the blood deforms or deflects flap portion 1577 away from skirt 1592, thereby forming a channel or passageway through which blood is permitted to flow into each pocket or compartment formed by skirt 1592. Once the pressure drops, polymer membrane 1581 springs back or returns to the closed configuration in which membrane 1581 covers and seals opening 1578, thereby trapping blood within each pocket to form a seal around the outer perimeter of the prosthesis.

In the embodiment of FIG. 13, anti-paravalvular leakage component 1390 is coupled to outer surface 103 of heart valve prosthesis 100 along constriction region 117 thereof, described with respect to FIG. 1 above. When deployed, anti-paravalvular leakage component 1390 may be positioned in situ at the native valve annulus, slightly above the valve annulus, slightly below the valve annulus, or some combination thereof. Since the annular anti-paravalvular leakage component is coupled to outer surface 103 of heart valve prosthesis 100, longitudinal placement and/or the size and shape thereof is flexible and may be adjusted or adapted according to each application and to a patient's unique needs. For example, depending on the anatomy of the particular patient, the anti-paravalvular leakage component may be positioned on heart valve prosthesis 100 so that in situ the anti-paravalvular leakage component is positioned between heart valve prosthesis 100 and the interior surfaces of the native valve leaflets, between heart valve prosthesis 100 and the interior surfaces of the native valve annulus, and/or between heart valve prosthesis 100 and the interior surfaces of the left ventricular outflow track (LVOT).

Although embodiments depicted herein illustrate one or more anti-paravalvular leakage components integrated onto a heart valve prosthesis configured for implantation within an aortic valve, it would be obvious to one of ordinary skill in the art that the anti-paravalvular leakage components as described herein may be integrated onto a heart valve prosthesis configured for implantation implanted within other heart valves, such as a mitral valve or a pulmonary valve.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A transcatheter valve prosthesis comprising:
a tubular stent having a compressed configuration for delivery within a vasculature and an expanded configuration for deployment within a native heart valve;
a prosthetic valve component disposed within and secured to the tubular stent; and
an anti-paravalvular leakage component coupled to and encircling an outer surface of the tubular stent, the anti-paravalvular leakage component including
a skirt formed of a flexible material and having a first edge coupled to the tubular stent and an opposing second edge not coupled to the tubular stent, and
an elongated strand having a first end, a second end, and a body extending between the first and second ends, the second end of the elongated strand being slidingly positioned over the body of the elongated strand such that the body of the elongated strand includes a radially expandable control ring that is coupled to the second edge of the skirt and a tether extending from the radially expandable control ring, wherein the first end of the elongated strand is configured to be pulled to move the second end of the elongated strand along the body of the elongated strand in order to selectively contract a diameter of the radially expandable control ring in situ and wherein the first end of the elongated strand is also configured to be pushed to move the second end of the elongated strand along the body of the elongated strand in order to selectively expand a diameter of the radially expandable control ring in situ.

2. The transcatheter valve prosthesis of claim 1, wherein the second end of the elongated strand is slidingly positioned over the body of the elongated strand via a series of interlocking teeth.

3. The transcatheter valve prosthesis of claim 1, wherein the body of the elongated strand includes at least one weakened area that breaks apart when force is applied thereto such that at least a portion of the tether is configured to be disconnected from the radially expandable control ring, the at least one weakened area being positioned along the tether.

4. The transcatheter valve prosthesis of claim 3, wherein the body of the elongated strand includes a plurality of weakened areas that break apart when force is applied thereto, the weakened areas being positioned between adjacent pairs of interlocking teeth in a series of interlocking teeth.

5. The transcatheter valve prosthesis of claim 3, wherein the at least one weakened area is a short segment of the elongated strand having a smaller diameter than the remaining length of the elongated strand.

6. The transcatheter valve prosthesis of claim 3, wherein the at least one weakened area includes a plurality of perforations.

* * * * *